United States Patent [19]

Hill et al.

[11] 4,125,710

[45] Nov. 14, 1978

[54] METHOD FOR PREPARING AURANOFIN

[75] Inventors: David T. Hill, North Wales, Pa.; Ivan Lantos, Blackwood, N.J.; Blaine M. Sutton, Hatboro, Pa.

[73] Assignee: Smithkline Corporation, Philadelphia, Pa.

[21] Appl. No.: 811,794

[22] Filed: Jun. 30, 1977

[51] Int. Cl.² ............................................. C07H 23/00
[52] U.S. Cl. .................................... 536/121; 424/180; 536/4; 536/122
[58] Field of Search .................................. 536/4, 121

[56] References Cited

U.S. PATENT DOCUMENTS 3,635,945  1/1972  Nemeth et al. ........................ 536/4

OTHER PUBLICATIONS

Sutton et al., J. Med. Chem. 15, 1095 (1972).

Primary Examiner—Johnnie R. Brown
Assistant Examiner—Blondel Hazel
Attorney, Agent, or Firm—William H. Edgerton

[57] ABSTRACT

Bis(triethylphosphine)gold salts are advantageous agents for preparing auranofin.

6 Claims, No Drawings

METHOD FOR PREPARING AURANOFIN

This method is based on the use of a certain series of gold complexes as agents for preparing various sugar thio(triethylphosphine)gold complexes including auranofin. The compounds are bis(triethylphosphine)-gold(I+) salts. The chloride or bromides are most often used but any stable anion may be present in the salt.

Auranofin is an orally active antiarthritic agent which is useful in man [J. Med. Chem., 15, 1095 (1972); U.S. Pat. No. 3,635,945]. In these references auranofin and its congeners are prepared by reacting an alkali metal salt of a 1-thio-β-D-glucopyranose with a trialkylphosphine-gold halide. The reaction of bis(triethylphosphine)gold salts with thiosugars is believed unexpected.

The bis tertiary-phosphinegold salts (II below in process A) unexpectedly have been found to be very reactive and can be substituted in reactions known to the art for tertiary-phosphinegold chloride or bromide with advantage. The bisphosphinegold complexes used in this invention in addition may enter into reactions in which the corresponding monophosphinegold complex may either fail to react or react slowly. The chief advantage the bisphosphinegold complexes have is that of being soluble in hydroxylic solvent systems such as aqueous ethanol in which the monophosphinegold complexes are of little practical use because of low solubility. For this reason a number of synthetic applications of bis-phosphinegold salts are now available to the art.

Illustrative of this invention is the following:

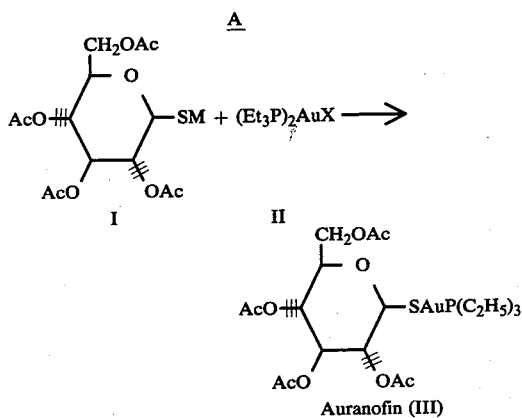

in which:
Ac is acetyl;
M is a stable common cation such as an alkali metal for example potassium or sodium, ammonium, lead, silver or copper or may be —S—R.
X is a stable common anion for example a halide such as chloride, bromide, iodide, nitrate (—NO₃), a thiocyanate (—SCN), perchlorate (—ClO₄), boron tetrafluoride (—BF₄) or trifluoroacetate (CF₃CO₂—); and
R is a sugar or hydrocarbon moiety of a symmetrical or unsymmetrical disulfide. Preferably R is 2,3,4,6-tetra-O-acetyl-β-D-glucopyranosylthio, that is, the symmetrical disulfide which yields auranofin (III).

The reactions of this invention are carried out by allowing the sugar containing thio compound (I) and the bis tertiary-phosphinegold salt (II) to react in a solvent in which the reactants are soluble. Such solvents may be a common halogenated hydrocarbon solvent such as carbon tetrachloride, chloroform, methylene chloride, acetone, dioxane, ethyl ether, dimethylformamide, dimethylacetamide, dimethylsulfoxide, dimethylcarbonate, benzenoic solvents, lower alkanol solvents such as methanol, ethanol or isopropanol, as well as aqueous mixtures of organic solvents miscible with water. The hydroxylic solvents such as aqueous methanol or ethanol are most conveniently used when M is a cation especially an inorganic one such as the preferred sodium or potassium ions. When M is such that compound I is a disulfide the halohydrocarbon solvents such as methylene chloride are most conveniently used.

The reaction is carried out over a range of temperatures depending on the reactivity of the reagents, the solvent and the size of the run. From 0° for the aqueous alcoholic mixtures up through ambient temperature and up to 75° may be used for from ½ hour to several days depending on reactivity of the starting material and the reaction conditions. Most conveniently, when an organic solvent is used as with a disulfide, a range of temperatures from ambient up to the boiling point of the reaction mixture for from 4 days to several hours are used. For all practical purposes, temperatures from 0°–50° are of most use.

In the reaction, other bis(tertiaryphosphine)gold salts may be used such as a bis(triphenylphosphine)gold bromide, bis(tribenzylphosphine)gold bromide or others. These are prepared by methods reported in Chem. Abst. 77, 147108, Chem. Abst. 73, 72615 or Chem. Abst. 74, 18869.

The sugar thio salts (I, M is a cation) are also known to the art and are preferably reacted with bis(triethylphosphine)gold chloride or bromide in aqueous ethanol, methanol or isopropanol. The sodium and potassium salts are preferred. These may be used as isolated starting materials or generated in situ in the reaction media. Thus convenient applicability of the bisphosphinegold salts to a number of reactions with advantage is largely due to the solubility of the bis(triethylphosphine)gold salts in aqueous alcohol.

The disulfide reactants (I, M is an organic thio moiety) are also known to the art with bis(2,3,4,6-tetra-O-acetyl-β-D-glucopyranosyl)disulfide being the most useful for preparing auranofin.

The following examples are illustrative of the practice of this invention. All temperatures are Centigrade.

EXAMPLE 1

Solutions of 1.66 g (0.012 mole) of potassium carbonate in 20 ml of water, 5.3 g (0.011 mole) of 2-(2,3,4,6-tetra-O-acetylglucopyranosyl)thiopseudourea hydrobromide in 30 ml of water and 5.15 g (0.011 mole) of bis(triethylphosphine)gold(I+) chloride in 30 ml of water were mixed together stepwise at 0° C. After the stirred mixture warmed to room temperature it was extracted with chloroform (4 × 50 ml). The combined extracts were washed with water (2 × 30 ml), dried (magnesium sulfate), filtered and the filtrate concentrated under reduced pressure to give 6.7 g of residual oil. Column chromatography (silica gel, chloroform) of the oil gave, after crystallization from ethanol, 3.1 g (42%) of S-triethylphosphinegold 2,3,4,6-tetra-O-acetyl-1-thio-β-D-glucopyranoside, m.p. 104°–108°; $[\alpha]_D^{25}$ (1% methanol) = −54.2°.

EXAMPLE 2

A chloroform solution (25 ml) of 1.2 g (2.6 mmoles) of bis(triethylphosphine)gold chloride and 2.0 g (2.6 mmoles) of bis(2,3,4,6-tetra-O-acetyl-β-D-glucopyranosyl)disulfide [Methods in Carbohydrate Chemistry, Vol. 2, 436 (1963)] was stirred 4 days at room temperature and the solvent removed at reduced pressure. Chromatography of the residue (silica gel, benzene-chloroform 0° to 100°) gave, after recrystallization from methanol-water, auranofin, m.p. 105°–7°; $[\alpha]_D^{25} = -52.1°$ (1% methanol).

EXAMPLE 3

A pyridine solution (100 ml) of 35 g (0.096 mole) of 2,3,4,6-tetra-O-acetyl-1-thio-β-D-glucopyranose [Methods in Carbohydrate Chemistry, Vol. 2, 436 (1963)] and 28 g (0.10 mole) of triphenylmethyl chloride was stirred at room temperature for 12 hours. The solution was filtered and the pyridine removed at reduced pressure. The residue was dissolved in chloroform (350 ml), washed with water (5 × 100 ml) and the chloroform solution dried in magnesium sulfate. The solvent was removed at reduced pressure and the residue dissolved in methanol and cooled to give 17 g (29%) of crystalline 2,3,4,6-tetra-O-acetyl-1-S-trityl-1-thio-β-D-glucopyranose, m.p. 177°–179°; $[\alpha]_D^{25}$ (1% methanol) = −37.8°.

A methanol solution (30 ml) of 0.84 g (4.9 mmoles) of silver nitrate and 3.0 g (4.9 mmoles) of 2,3,4,6-tetra-O-acetyl-1-S-trityl-1-thio-β-D-glucopyranose was stirred at 35° for 30 minutes. The solution was then diluted to 100 ml with ether and cooled at −20° overnight. The resulting precipitate was removed by filtration, washed with ether and dried to give 1.94 g (83%) of 2,3,4,6-tetra-O-acetyl-1-S-silver-1-thio-β-D-glucopyranose, m.p. 123°–128°.

A methanol solution (35 ml) of 1.94 g (4.1 mmols) of 2,3,4,6-tetra-O-acetyl-1-S-silver-1-thio-β-D-glucopyranose and 4.1 mmoles of bis(triethylphosphine)gold bromide is stirred at room temperature for 1 hour. After filtration, the solvent is evaporated in vacuo. The residue is purified over silica gel with chloroform to give auranofin.

What is claimed is:

1. The method of preparing auranofin comprising reacting a compound of the formula:

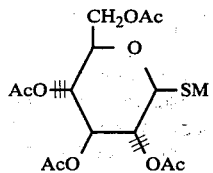

in which M is a stable cation selected from the group consisting of an alkali metal, ammonium, lead, silver or copper cation or

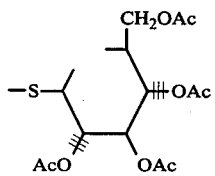

and Ac is acetyl, with a compound of the formula:

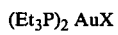

in which X is a stable common anion selected from the group consisting of a halide, nitrate, thiocyanate, perchlorate, boron tetrafluoride or trifluoroacetate; in a solvent which is inert to the reactants and in which the reactants are soluble.

2. The method of claim 1 in which M is potassium or sodium and X is chloride or bromide.

3. The method of claim 2 in which the solvent is aqueous methanol or ethanol and the reaction is carried out at about 0° to ambient temperature.

4. The method of claim 1 in which M is

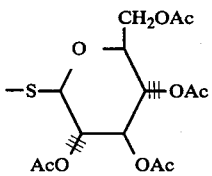

and X is chloride or bromide.

5. The method of claim 4 in which the solvent is chloroform or methylene chloride at from room temperature up to the boiling point of the reaction mixture.

6. In the method of preparing auranofin, the improvement comprising the use of a bis(tertiary)gold salt as starting material.

* * * * *